United States Patent
Ma et al.

(10) Patent No.: US 11,306,338 B2
(45) Date of Patent: Apr. 19, 2022

(54) TAGATOSE-6-PHOSPHATE 4-EPIMERASE AND APPLICATION THEREOF

(71) Applicant: Tianjin Institute of Industrial Biotechnology, Chi, Tianjin (CN)

(72) Inventors: Yanhe Ma, Tianjin (CN); Yuanxia Sun, Tianjin (CN); Yunjie Li, Tianjin (CN); Jiangang Yang, Tianjin (CN)

(73) Assignee: TIANJIN INSTITUTE OF INDUSTRIAL BIOTECHNOLOGY, CHINESE ACADEMY OF SCIENCES, Tianjin (CN)

(*) Notice: Subject to any disclaimer, the term of this patent is extended or adjusted under 35 U.S.C. 154(b) by 0 days.

(21) Appl. No.: 16/761,145

(22) PCT Filed: Dec. 28, 2018

(86) PCT No.: PCT/CN2018/124999
§ 371 (c)(1),
(2) Date: May 1, 2020

(87) PCT Pub. No.: WO2019/086054
PCT Pub. Date: May 9, 2019

(65) Prior Publication Data
US 2021/0180101 A1   Jun. 17, 2021

(30) Foreign Application Priority Data
Nov. 2, 2017   (CN) .......................... 201711066091.9

(51) Int. Cl.
*C12N 15/52* (2006.01)
*C12P 19/24* (2006.01)
*C12N 15/63* (2006.01)
*C12P 19/02* (2006.01)

(52) U.S. Cl.
CPC .............. *C12P 19/24* (2013.01); *C12N 15/52* (2013.01); *C12N 15/63* (2013.01); *C12P 19/02* (2013.01); *C12Y 204/01001* (2013.01); *C12Y 207/01101* (2013.01); *C12Y 503/01009* (2013.01); *C12Y 504/02002* (2013.01)

(58) Field of Classification Search
CPC . C12N 9/90; C12N 9/1205; C12Y 503/01009
See application file for complete search history.

(56) References Cited

U.S. PATENT DOCUMENTS

2016/0186162 A1   6/2016   Oh et al.

FOREIGN PATENT DOCUMENTS

| | | |
|---|---|---|
| CN | 105431541 A | 3/2016 |
| CN | 106399427 A | 2/2017 |
| CN | 107109394 A | 8/2017 |
| CN | 107988286 A | 5/2018 |
| WO | WO-2017059278 A1 * | 4/2017 ..... C12Y 207/01144 |

OTHER PUBLICATIONS

Accession No. A9CES6 (Year: 2008).*
"Hypothetical Protein [*Thermoanaerobacter Indiensis*]" NCBI Reference Sequence WP_019907213.1, Jun. 29, 2013.

* cited by examiner

*Primary Examiner* — Tekchand Saidha
(74) *Attorney, Agent, or Firm* — Tarolli, Sundheim, Covell & Tummino LLP

(57) ABSTRACT

Disclosed is a new tagatose 6-phosphate 4-epimerase, which is capable of converting fructose 6-phosphate into tagatose 6-phosphate and vice versa. Also disclosed is an application of the enzyme in tagatose production.

2 Claims, 4 Drawing Sheets

Specification includes a Sequence Listing.

SEQUENCE LISTING

```
<160> NUMBER OF SEQ ID NOS: 2

<210> SEQ ID NO 1
<211> LENGTH: 446
<212> TYPE: PRT
<213> ORGANISM: Thermoanaerobacter indiensis

<400> SEQUENCE: 1

Met Asn Thr Glu His Pro Leu Lys Asn Val Val Lys Leu Gln Lys Lys
1               5                   10                  15

Gly Ile Pro Ile Gly Ile Tyr Ser Val Cys Ser Ala Asn Glu Ile Val
            20                  25                  30

Ile Gln Val Ala Met Glu Lys Ala Leu Ser Met Asp Ser Tyr Val Leu
        35                  40                  45

Ile Glu Ala Thr Ala Asn Gln Val Asn Gln Tyr Gly Gly Tyr Thr Asn
    50                  55                  60

Met Lys Pro Ile Asp Phe Arg Asp Phe Val Tyr Ser Ile Ala Lys Arg
65                  70                  75                  80

Ile Asn Phe Pro Glu Asn Arg Ile Ile Leu Gly Gly Asp His Leu Gly
                85                  90                  95

Pro Leu Pro Trp Lys Asn Gln Gln Ala Lys Lys Ala Met Glu Glu Ala
            100                 105                 110

Lys Glu Leu Val Lys Gln Phe Val Met Ala Gly Phe Thr Lys Ile His
        115                 120                 125

Val Asp Thr Ser Met Phe Leu Gly Asp Asp Asn Ile Asn Ile Lys Leu
    130                 135                 140

Asp Thr Glu Thr Ile Ala Glu Arg Gly Ala Ile Leu Val Ser Val Ala
145                 150                 155                 160

Glu Arg Ala Phe Glu Glu Leu Lys Lys Ser Asn Pro Tyr Ala Leu His
                165                 170                 175

Pro Val Tyr Val Ile Gly Ser Glu Val Pro Val Pro Gly Gly Ser Gln
            180                 185                 190

Lys Glu Asn Asn Asn Glu Ile Gln Val Thr Lys Pro Ala Asp Phe Glu
        195                 200                 205

Glu Thr Val Glu Val Tyr Lys Ser Thr Phe Tyr Lys Tyr Gly Leu Gly
    210                 215                 220

Asn Ala Trp Glu Asp Val Ala Val Val Gln Pro Gly Val Glu
225                 230                 235                 240

Phe Gly Val Glu Asn Ile His Glu Tyr Asp His Gln Gln Ala Glu Asn
                245                 250                 255

Leu Val Ser Ala Leu Lys Lys Tyr Pro Asn Leu Val Phe Glu Ala His
            260                 265                 270

Ser Thr Asp Tyr Gln Pro Ala Lys Leu Leu Lys Glu Met Val Arg Asp
        275                 280                 285

Gly Phe Ala Ile Leu Lys Val Gly Pro Glu Leu Thr Phe Ala Leu Arg
    290                 295                 300
```

```
Glu Gly Leu Phe Ala Leu Asn Ile Ile Glu Lys Glu Leu Phe Lys Asp
305                 310                 315                 320

Asn His Asp Ile Glu Met Ser Asn Phe Ile Asp Ile Leu Asp Thr Ala
                325                 330                 335

Met Leu Asn Asn Pro Lys Tyr Trp Glu Gln Tyr Tyr Tyr Gly Asp Asp
            340                 345                 350

Asn Lys Ile Arg Ile Ala Arg Lys Tyr Ser Tyr Ser Asp Arg Cys Arg
        355                 360                 365

Tyr Tyr Leu Ile Glu Asn Glu Val Arg Ala Ser Met Ser Arg Leu Phe
    370                 375                 380

Lys Asn Leu Thr Asn Val Glu Ile Pro Leu Thr Leu Ile Ser Gln Tyr
385                 390                 395                 400

Met Pro Ile Gln Tyr Glu Lys Ile Arg Met Gly Leu Leu Lys Asn Asp
                405                 410                 415

Pro Glu Asn Leu Val Lys Asp Lys Ile Gly Asn Cys Ile Asp Lys Tyr
            420                 425                 430

Leu Tyr Ala Thr Asn Pro Thr Ser Gly Glu Phe Lys Leu Ile
        435                 440                 445
```

<210> SEQ ID NO 2
<211> LENGTH: 1341
<212> TYPE: DNA
<213> ORGANISM: Thermoanaerobacter indiensis

<400> SEQUENCE: 2

```
atgaacaccg aacatccgct gaaaaatgtg gttaaactgc agaaaaaagg tattccgatt      60
ggcatctata gtgtgtgtag cgccaatgaa attgttattc aggttgccat ggaaaaagcc     120
ctgagtatgg atagttatgt tctgattgaa gccaccgcca atcaggttaa tcagtatggt     180
ggctatacca atatgaaacc gattgatttt cgcgattttg tgtatagtat cgccaaacgt     240
attaattttc cggaaaatcg cattattctg ggtggcgatc atctgggccc gctgccgtgg     300
aaaaatcagc aggccaaaaa agcaatggaa gaagccaaag aactggttaa acagtttgtg     360
atggccggct ttaccaaaat tcatgttgat accagcatgt ttctgggtga cgataatatt     420
aatatcaagc tggataccga accattgcaa gaacgcggtg ccattctggt tagtgttgcc     480
gaacgtgcct ttgaagaact gaaaaaatct aatccgtacg ccctgcatcc ggtgtatgtt     540
attggcagcg aagttccggt gccgggcggc tcacagaaag aaaataataa tgaaatccag     600
gtgaccaaac cggcagattt tgaagaaacc gttgaagttt ataagagcac cttttataag     660
tacggcctgg gtaatgcatg ggaagatgtg gttgccgtgg ttgtgcagcc gggcgttgaa     720
tttggtgtgg aaaatattca tgaatacgat catcagcagg cagaaaatct ggttagcgcc     780
ctgaaaaaat atccgaatct ggtgtttgaa gcacatagca ccgattatca gccggccaaa     840
ctgctgaaag aaatggtgcg cgatggtttt gccattctga agtgggccc ggaactgacc      900
tttgccctgc gtgaaggtct gtttgccctg aatattattg aaaaagaact gtttaaggac     960
aaccatgata ttgaaatgag taatttcatc gacatcctgg ataccgcaat gctgaataat    1020
ccgaaatatt gggaacagta ttactatggc gatgataata gattcgcat tgcccgcaaa     1080
tatagctata gtgatcgctg ccgttattat ctgattgaaa atgaagtgcg tgcaagcatg    1140
agtcgcctgt ttaaaaatct gaccaatgtg gaaattccgc tgaccctgat tagccagtat    1200
atgccgattc agtatgaaaa aattcgtatg ggcctgctga aaaatgatcc ggaaaatctg    1260
```

```
gtgaaagata aaattggcaa ttgtattgac aagtacctgt atgccaccaa tccgaccagc    1320
ggtgaattca aactgattta a                                              1341
```

TAGATOSE-6-PHOSPHATE 4-EPIMERASE AND APPLICATION THEREOF

FIELD OF THE INVENTION

The present invention relates to the field of genetic engineering and biocatalysis, and provides a new tagatose 6-phosphate 4-epimerase, which has the function of epimerizing the 4-position carbon of fructose 6-phosphate, converting fructose 6-phosphate into tagatose 6-phosphate and converting tagatose 6-phosphate into fructose 6-phosphate. The present invention also provides the application of the enzyme in the production of tagatose.

BACKGROUND OF THE INVENTION

The 4-position epimerization of 6-carbon sugar plays an important role in the production of rare sugars and their derivatives, for example, a Korean patent (application number: WO2015016544A1) reported that fructose 6-phosphate is subjected to epimerization at 4 position to be converted into tagatose 6-phosphate, and then tagatose 6-phosphate is dephosphorized into tagatose. The tagatose 6-phosphate 4-epimerase reported in this patent is fructose 1,6-phosphate aldolase from *E. coli*, which has two different sets of catalytic amino acids to catalyze different reactions (Sci Rep 2017; 7: 1934), wherein one set of catalytic amino acids catalyzes the condensation of fructose 1,6-diphosphate to glyceraldehyde 3-phosphate and dihydroxyacetone phosphate, and the other set of catalytic amino acids catalyzes the conversion of tagatose 6-phosphate to fructose 6-phosphate. The two sets of catalytic amino acids do not interfere with each other. Mutation of amino acids that catalyze the condensation of fructose 1,6-diphosphate to glyceraldehyde 3-phosphate and dihydroxyacetone phosphate will not affect the enzyme activity that catalyzes the conversion of tagatose 6-phosphate to fructose 6-phosphate. However, due to the low thermal stability of the enzyme, it is not suitable for large-scale production of tagatose. In addition, when Wichelecki et al. studied the metabolism of azetitol and galactitol in *Agrobacterium tumefaciens*, they found that an enzyme encoded by the gene Atu3167 can catalyze the conversion of tagatose 6-phosphate to fructose 6-phosphate (J Biol Chem 2015; 290:28963-28976). However, the thermal stability of the enzyme is also not high, which is not suitable for large-scale production of tagatose. Therefore, in the preparation of rare sugars, especially in the process of large-scale production of rare sugars, there is an urgent need for a tagatose 6-phosphate 4-epimerase with high thermal stability, and capable of completing 4-position epimerization in simple process steps; the thermostable enzyme can be applied to an in vitro multi-enzyme system to produce tagatose.

SUMMARY OF THE INVENTION

In view of this, in a first aspect, the present invention provides a tagatose 6-phosphate 4-epimerase (TiT4E) for catalyzing mutual conversion between fructose 6-phosphate and tagatose 6-phosphate, wherein the tagatose 6-phosphate 4-epimerase is selected from the group consisting of:

(a) a protein having the amino acid sequence set forth in SEQ ID NO: 1; or (b) a derived protein formed by substitution, deletion or addition of one or more amino acid residues in the protein having the amino acid sequence set forth in SEQ ID NO: 1, and having an activity of catalyzing mutual conversion between fructose 6-phosphate and tagatose 6-phosphate; or (c) a derived protein having a sequence comprising the sequence of the protein described in (a) or (b); or (d) a derived protein having an amino acid sequence of ≥60% (preferably ≥80%, more preferably ≥90%) identity to the amino acid sequence set forth in SEQ ID NO: 1, and having an activity of catalyzing mutual conversion between fructose 6-phosphate and tagatose 6-phosphate.

In another preferred embodiment, the tagatose 6-phosphate 4-epimerase is derived from *Thermoanaerobacter indiensis*.

In another preferred embodiment, the amino acid sequence of the tagatose 6-phosphate 4-epimerase is set forth in SEQ ID NO: 1.

In a second aspect, the present invention provides a nucleotide sequence, the nucleotide sequence is selected from the group consisting of (a) a nucleotide sequence encoding the protein set forth in SEQ ID NO: 1; or (b) a nucleotide sequence set forth in SEQ ID NO: 2; or (c) a nucleotide sequence of ≥50% (preferably ≥80%, more preferably ≥90%) identity to the nucleotide sequence set forth in SEQ ID NO: 2; or (d) a nucleotide sequence which is complementary (preferably completely complementary) to the nucleotide sequence of any one of (a) to (c).

In another preferred embodiment, the nucleotide sequence is set forth in SEQ ID NO: 2.

In a third aspect, the present invention provides a vector comprising the polynucleotide according to the second aspect of the present invention.

In a fourth aspect, the present invention provides a host cell comprising the vector according to the third aspect of the present invention, or having the polynucleotide according to the second aspect of the present invention integrated into its genome.

In another preferred embodiment, the host cell is a prokaryotic cell or an eukaryotic cell.

In another preferred embodiment, the host cell is a prokaryotic cell, such as a bacterial cell, preferably, *E. coli*.

In a fifth aspect, the present invention provides a use of the tagatose 6-phosphate 4-epimerase (TiT4E) according to the first aspect of the present invention or a derived protein thereof or the host cell according to the fourth aspect in the catalysis of mutual conversion between fructose 6-phosphate and tagatose 6-phosphate.

In a sixth aspect, the present invention provides a use of the tagatose 6-phosphate 4-epimerase (TiT4E) according to of the first aspect of the present invention or the vector according to the third aspect or the host cell according to the fourth aspect in the construction of an in vitro multi-enzyme catalytic system to prepare tagatose.

In another preferred embodiment, the multi-enzyme catalytic system comprises α-glucan phosphorylase (αGP), phosphoglucomutase (PGM), phosphoglucoisomerase (PGI), tagatose 6-phosphate 4-epimerase (TiT4E), and tagatose 6-phosphate phosphatase (T6P).

In another preferred embodiment, the multi-enzyme catalytic system uses starch or maltodextrin as a substrate to prepare tagatose.

The polynucleotide sequence of the present invention can be obtained by the following methods: 1) obtaining the double-stranded DNA sequence from amplification of genomic DNA; 2) chemically synthesizing a DNA sequence to obtain the double-stranded DNA of the polypeptide.

In the present invention, a polynucleotide sequence encoding the thermostable tagatose 6-phosphate 4-epimerase (TiT4E) can be inserted into a vector to constitute a vector comprising the polynucleotide of the present invention. The term "vector" refers to a bacterial plasmid, a bacteriophage, a yeast plasmid, a plant cell virus, a mammalian cell virus such as adenovirus, retrovirus, or other vectors as well known in the art. Vectors suitable for use in the present invention include, but are not limited to: T7 promoter-based expression vectors expressed in bacteria (Gene, 1987, 56: 125), such as pET20b vector; pMSXND expression vector expressed in mammalian cells (J Bio Chem. 263: 3521, 1988) and vectors derived from baculovirus expressed in insect cells. In brief, any plasmid and vector can be used to construct a recombinant expression vector as long as it can replicate and be stable in the host. An important feature of an expression vector is that it usually contains an origin of replication, a promoter, a marker gene, and a translation regulatory element. Methods well known to those skilled in the art can be used to construct an expression vector comprising the polynucleotide sequence of TiT4E and an appropriate transcription/translation regulatory element. These methods include in vitro recombinant DNA technology, DNA synthesis technology, in vivo recombinant technology, and the like. (Molecular Cloning, a Laboratory Manual, cold Spring Harbor Laboratory. New York, 1989). The polynucleotide sequence can be effectively linked to an appropriate promoter in an expression vector to guide mRNA synthesis. Representative examples of the promoter are lac or trp promoter of *E. coli*; PL promoter of λ phage; eukaryotic promoters including CMV immediate early promoter, HSV thymidine kinase promoter, early and late SV40 promoter, retroviral LTRs and other known promoters that can control gene expression in prokaryotic or eukaryotic cells or their viruses.

In addition, the expression vector preferably comprises one or more selectable marker genes to provide phenotypic traits for selection of transformed host cells, such as ampicillin resistance for *E. coli*, tetracycline, kanamycin, and the like, or dihydrofolate reductase, neomycin resistance and green fluorescent protein (GFP) for use in eukaryotic cell culture.

Those of ordinary skill in the art know how to select appropriate vectors/transcription regulatory elements (such as promoters, enhancers, etc.) and selectable marker genes.

In the present invention, a polynucleotide encoding the tagatose 6-phosphate 4-epimerase (TiT4E) or a vector comprising the polynucleotide can be transformed or transduced into a host cell to constitute a genetically engineered host cell comprising the polynucleotide or vector. The term "host cell" refers to prokaryotic cells, such as bacterial cells; or lower eukaryotic cells, such as yeast cells; or higher eukaryotic cells, such as mammalian cells. Representative examples comprise *E. coli, Streptomyces*; bacterial cells such as *Salmonella typhimurium*; fungal cells such as yeast; plant cells; insect cells such as fly S2 or Sf9; animal cells such as CHO, COS or Bowes melanoma cells.

Transformation of a host cell with the polynucleotide sequence of the present invention or the vector comprising the polynucleotide sequence can be performed by conventional techniques well known to those skilled in the art. When the host is a prokaryotic organism such as *E. coli*, competent cells that can absorb DNA can be harvested after the exponential growth phase, and treated with the $CaCl_2$ method. The procedures used are well known in the art. Alternatively, $MgCl_2$ may be used. If necessary, transformation can also be carried out by electroporation. When the host is a eukaryote, the following DNA transfection methods can be used: calcium phosphate co-precipitation method, or conventional mechanical methods such as microinjection, electroporation, liposome packaging, and the like.

Through conventional recombinant DNA technology, the polynucleotide sequence of the present invention can be used to express or produce recombinant tagatose 6-phosphate 4-epimerase (TiT4E). Generally, the following steps are comprised: (1) transforming or transducing suitable host cells with the polynucleotide encoding tagatose 6-phosphate 4-epimerase (TiT4E) according to the present invention, or with a vector comprising the polynucleotide; (2) culturing the host cells in a suitable culture medium; and (3) isolating and purifying the protein from the cells.

In step (2), according to the host cells used, the culture medium used in the culturing may be selected from various conventional culture media. The culturing is carried out under conditions suitable for the growth of host cells. When the host cells grow to an appropriate cell density, the selected promoter is induced by an appropriate method (such as temperature conversion or chemical induction), and the cells are further cultured for a period of time.

In step (3), the protein may be comprised in the cell, expressed on the cell membrane, or secreted out of the cell. If necessary, the recombinant protein can be isolated and purified by various separation methods using its physical, chemical and other characteristics. These methods are well known to those skilled in the art. These methods include but are not limited to conventional renaturation treatment, treatment with protein precipitation agents (salting out method), centrifugation, osmotic disruption, ultrasonic treatment, ultracentrifugation, molecular sieve chromatography (gel filtration), adsorption chromatography, ion exchange chromatography, high performance liquid chromatography (HPLC) and various other liquid chromatographic techniques and combinations of these methods.

Unless otherwise specified, the following terms used in this description and claims have the following meanings. The term "nucleic acid sequence" refers to oligonucleotides, nucleotides or polynucleotides and fragments or portions thereof, and can also refers to genomic or synthetic DNA or RNA, which can be single-stranded or double-stranded, representing a sense strand or an antisense strand. Similarly, the term "amino acid sequence" refers to oligopeptides, peptides, polypeptides or protein sequences and fragments or portions thereof. When the "amino acid sequence" in the present invention refers to the amino acid sequence of a naturally occurring protein molecule, such a "polypeptide" or "protein" is not meant to limit the amino acid sequence to the complete natural amino acids associated with the protein molecule.

A derived protein refers to an amino acid sequence with a change in one or more amino acids or nucleotides. The change may include deletion, insertion or substitution of amino acids in the amino acid sequence. The derived protein can have a "conservative" change, in which the amino acid for substitution has structural or chemical properties similar to those of the original amino acid, such as substituting isoleucine with leucine. The derived protein can also have a non-conservative change, such as substituting glycine with tryptophan.

The term "deletion" refers to the deletion of one or more amino acids or nucleotides in an amino acid sequence or a nucleotide sequence.

The term "insertion" or "addition" refers to a change in an amino acid sequence or a nucleotide sequence that results in an increase of one or more amino acids or nucleotides compared to a naturally occurring molecule. "Substitution" refers to the replacement of one or more amino acids or nucleotides with different amino acids or nucleotides.

The term "complementary" or "complementarity" refers to the natural binding of polynucleotides by base pairing under allowable salt concentration and temperature conditions. For example, the sequence "C-T-G-A" can be bound to the complementary sequence "G-A-C-T". Two single-stranded molecules can be partially or completely complementary to each other. The degree of complementarity between nucleic acid strands has a significant effect on the efficiency and strength of hybridization between nucleic acid strands.

The term "identity percentage" refers to the percentage of sequences that are identical or similar in comparison of two or more amino acid sequences or nucleic acid sequences. Identity percentage can be determined by software, such as GeneDoc program.

DETAILED DESCRIPTION OF THE INVENTION

The present invention will be further described by combining the following specific examples. The advantages and characteristics of the present invention will become apparent as the description proceeds. However, it should be understood that the examples are only exemplary and are not intended to limit the scope of the present invention. Those skilled in the art should understand that the details and forms of the technical solutions of the present invention can be modified or replaced without departing from the spirit and scope of the present invention, and all these modifications or replacements fall within the protection scope of the present invention. It should be understood that these examples are only used to illustrate the present invention and are not intended to limit the scope of the present invention. The experimental methods without specific conditions indicated in the following examples generally follow the conventional conditions such as those described in Sambrook et al., Molecular Cloning: Laboratory Manual (New York: Cold Spring Harbor Laboratory Press, 1989), or the conditions recommended by the manufacturer.

Experimental Materials

Maltodextrin, a product from ALDRICH company, with a product number of 419672;

pET20b vector, Novagen, Madison, Wis.;

E. coli expression bacteria BL21 (DE3), Invitrogen, Carlsbad, Calif.;

Fructose 6-phosphate, a product from Sigma company, with a product number of F3627;

Tagatose 6-phosphate, a product from Sigma company, with a product number of 50661;

Example 1. Cloning of TiT4E Gene

The amino acid sequence of the polypeptide tagatose 6-phosphate 4-epimerase was obtained from NCBI (https://www.ncbi.nlm.nih.gov/). The NCBI Reference Sequence of the sequence was WP_019907213.1 (SEQ. No. 1), the polypeptide was named TiT4E, and TiT4E is annotated as a hypothetical protein on NCBI, and is classified as tagatose 6-phosphate kinase, which is an enzyme that phosphorylates tagatose under the action of ATP to generate tagatose 6-phosphate. Subsequently, Wuxi Qinglan Biotech Co., Ltd. (http://qinglanbiotech.com/) was commissioned to design the polynucleotide (DNA) sequence encoding the polypeptide based on the amino acid sequence, and to codon-optimize it for E. coli expression system. The optimized polynucleotide sequence is set forth in SEQ ID NO: 2.

Figure 2:
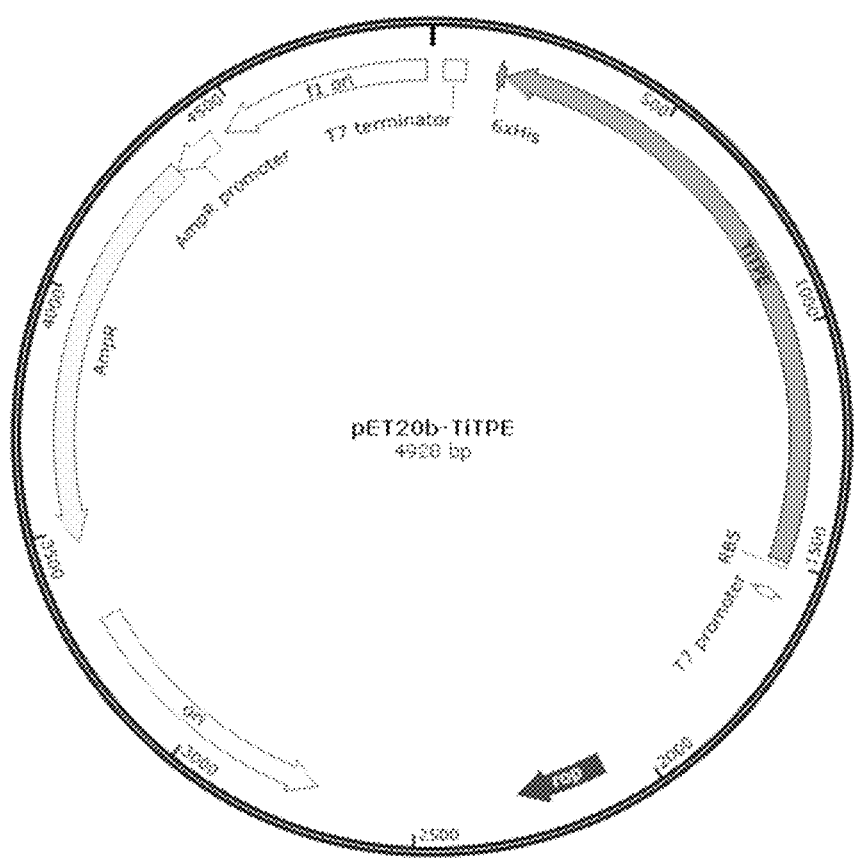
FIG. 2. A schematic diagram showing a vector of pET20b-TiT4E plasmid that can express TiT4E in E. coli.

Wuxi Qinglan cloned the codon-optimized sequence into pMV vector to form pMV-TiT4E plasmid. Subsequently, the TiT4E fragment was amplified by using forward primer GAAC<u>ATATG</u> AACACCGAACATCCGCTG (underlined part showing NdeI restriction site) and reverse primer CCG <u>CTCGAG</u>AATCAGTTTGAATTCACCGC (underlined part showing XhoI restriction site), and the pMV-TiT4E plasmid as a template, and after digestion with NdeI and XhoI, was ligated to the pET20b vector that was also digested with NdeI and XhoI, so as to obtain the pET20b-TiT4E expression vector (FIG. 2). In the expression vector, elements such as T7 promoter and T7 terminator were responsible for the expression of TiT4E. The expressed TiT4E had a 6×His tag at the C-terminal, and Ni-NTA resin can be used for protein purification.

Example 2. Expression and Purification of TiT4E

Figure 3:
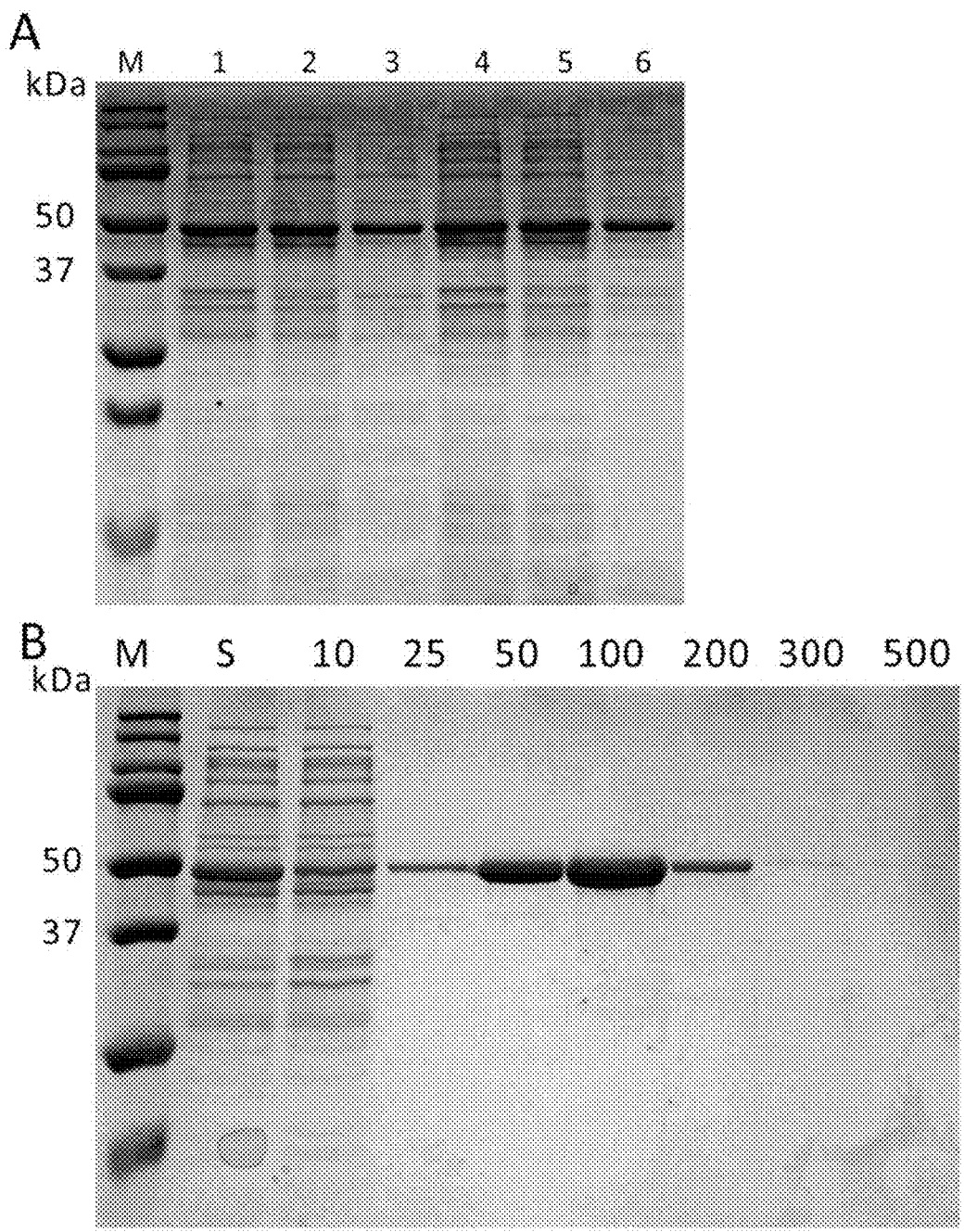
FIG. 3. (A) BL21 (DE3) E. coli comprising pET20b-TiT4E was induced for expression at different temperatures with IPTG at a final concentration of 100 μM, and partial purification was performed by subjecting the supernatant to heat treatment at 60° C. Lane M, protein markers, Lane 1, the cell disruption fluid in which the expression of TiT4E was induced at 37° C., Lane 2, the supernatant of the cell disruption fluid in which the expression of TiT4E was induced at 37° C., Lane 3, the supernatant after heat treatment of the supernatant of the cell disruption fluid in which the expression of TiT4E was induced at 37° C., Lane 4, the cell disruption fluid in which the expression of TiT4E was induced at 18° C., Lane 5, the supernatant of the disruption fluid of cells in which the expression of TiT4E was induced at 18° C., Lane 6, the supernatant after heat treatment of the supernatant of the disruption fluid of cells in which the expression of TiT4E was induced at 18° C. (B) Purification of soluble TiT4E protein with Ni-NTA, Lane M, protein markers, Lane S, the cell disruption supernatant of TiT4E, Lanes 20-500, which represent TiT4E eluted from buffer containing different concentrations of imidazole (20 mM to 500 mM).

The pET20b-TiT4E was transformed into E. coli BL21 (DE3), and the monoclones were selected and placed in 3 ml LB medium containing 100 μg/ml ampicillin, and cultured at 37° C. and 220 rpm overnight. 1 ml overnight bacteria were transferred to 200 ml LB medium containing 100 μg/ml ampicillin, and when an OD600 value reached about 0.8 at 37° C. and 220 rpm, isopropyl β-D-1-thiogalactopyranoside (IPTG) was added at a final concentration of 100 μM to induce protein expression at 37° C. and 18° C., respectively. The induction at 37° C. was carried out for 4 hours and the induction at 18° C. was carried out for 20 hours. After the induction, the cells were collected by centrifugation, re-suspended with 30 mM phosphate buffer (pH 7.0), and the cells were broken by ultrasound to obtain a cell disruption liquid. The expression level of enzyme was detected by SDS-PAGE, as shown by Lane 1 and Lane 4 in FIG. 3A. The cell disruption liquid was subjected to high-speed centrifugation (12000 rpm, 10 min), and the supernatant was also detected by SDS-PAGE, as shown by Lane 2 and Lane 5 in FIG. 3A. It can be seen that no matter induced at 18° C. or 37° C., the expression of TiT4E was almost soluble expression. Since TiT4E is derived from the thermotolerant bacterium *Thermoanaerobacter indiensis*, the supernatant of the cell disruption liquid was treated at 60° C. for 20 minutes for partial purification, and then the purification effect was detected using SDS-PAGE (Lane 3 and Lane 6 in FIG. 3A). It can be seen that the protein of interest was partially purified, but the purity was not high. Subsequently, the enzyme was purified using a Ni-NTA column. As shown in FIG. 3B, it can be seen that relatively pure TiT4E can be eluted by 30 mM phosphate buffer containing 50 mM to 200 mM imidazole. The TiT4E containing imidazole was dialyzed to remove excess imidazole and was used for enzyme activity assay in next step.

Example 3. Enzyme Activity Assay of TiT4E

Figure 4:
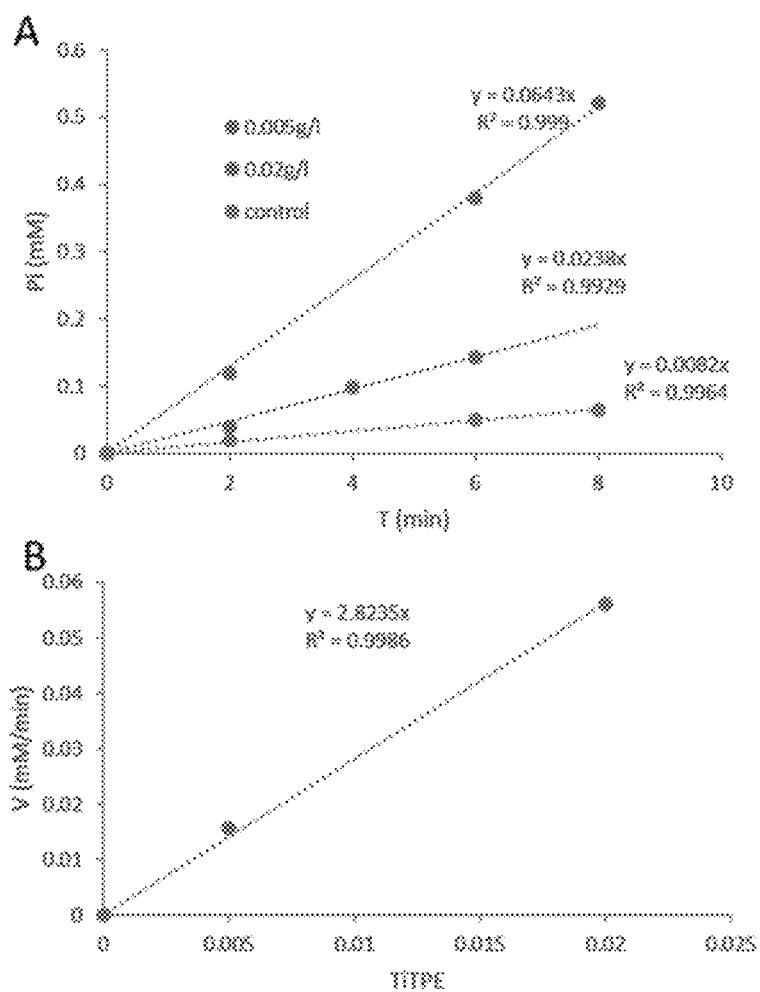
FIG. 4. The enzyme activity assay of TiT4E for converting fructose 6-phosphate to tagatose 6-phosphate.

The method for measuring the enzyme activity of TiT4E was as followed. A reaction system contained fructose 6-phosphate, tagatose 6-phosphate phosphatase, buffer, and magnesium ions, and the increased amount of inorganic phosphorus in the reaction system was measured after the reaction. Specifically, in a reaction system comprising 100 mM HEPES buffer, 10 mM fructose 6-phosphate, 10 U/ml tagatose 6-phosphatase (from *Archaeoglobus fulgidus*, the gene numbering on KEGG was AF_0444, the gene was also heterologously expressed in *E. coli*, and purified by Ni-NTA column to obtain a large amount of enzyme), 5 mM magnesium sulfate, 0.005 or 0.02 g/L TiT4E, the reaction was carried out at 60° C. for 8 minutes. After the reaction, the reaction was terminated by ice bath. The inorganic phosphorus ions released were measured using the method for measuring inorganic phosphorus as provided in the literature (Anal. Chem. 1956, 28, 1756-1759). Since tagatose 6-phosphate phosphatase also had a weak phosphorolysis effect on fructose 6-phosphate, the control experimental group was a reaction system without adding TiT4E. The inorganic phosphorus ions released during the reaction are shown in FIG. 4A. It can be seen that the enzyme reaction was a linear reaction, that is, the inorganic phosphorus ions released and the reaction time were proportional to the enzyme concentration. By plotting the concentration of the enzyme and the production rate of inorganic phosphorus ions (FIG. 4B), the enzyme activity of TiT4E for converting fructose 6-phosphate to tagatose 6-phosphate at 60° C. was calculated to be 2.82 U/mg. Therefore, the polypeptide TiT4E has the activity of converting fructose 6-phosphate to tagatose 6-phosphate. One unit of enzyme activity represents the amount of enzyme required to produce 1 μmol product in one minute.

Subsequently, the enzyme activity of TiT4E for converting tagatose 6-phosphate to fructose 6-phosphate was measured. In a reaction system comprising 100 mM HEPES buffer, 10 mM tagatose 6-phosphate, 5 mM magnesium sulfate, 0.005 or 0.02 g/L TiT4E, the reaction was carried out at 60° C. for 8 minutes. After the reaction, the reaction was terminated by ice bath. To the final sample, 1 U/ml phosphoglucoisomerase (PGI, purchased from Sigma, with a product number of P5381), 5 U/ml glucose 6-phosphate dehydrogenase (G6PDH, purchased from Sigma, with a product number of G6378), and 5 mM NAD$^+$ were added, and the reaction was carried out at 37° C. until OD340 no longer increased. The amount of the fructose 6-phosphate produced was calculated by the increased OD340. The enzyme activity of the polypeptide TiT4E for converting tagatose 6-phosphate to fructose 6-phosphate at 60° C. was 3.7 U/mg.

From this, it can be concluded that the protein having the amino acid sequence set forth in SEQ ID No: 1 had the enzyme activity for converting tagatose 6-phosphate to fructose 6-phosphate and vice versa, and the protein was defined as tagatose 6-phosphate 4-epimerase.

Example 4. Stability of TiT4E

The purified TiT4E was diluted into 30 mM phosphate buffer (pH 7.0), 5 mM magnesium sulfate ion to a final concentration of 0.1 mg/ml, and was treated at 70° C. for different periods of time (30 minutes to 6 hours). The residual activity of TiT4E for converting fructose 6-phosphate to tagatose 6-phosphate was then determined, and the stability of TiT4E at 70° C. was calculated from the residual activity. Through calculation, the $t_{1/2}$ time (the time when half of the enzyme activity is lost) of TiT4E at 70° C. was 4.7 hours. The result showed that the enzyme would lose 50% of its enzyme activity after being treated at 70° C. for 4.7 hours. Therefore, in the subsequent application of the enzyme in tagatose production, the temperature of the enzyme was reduced to 60° C. to ensure the long-term stability of the enzyme.

Example 5. Preparation of Tagatose by TiT4E

An in vitro multi-enzyme catalytic system comprising α-glucan phosphorylase (αGP), phosphoglucomutase (PGM), phosphoglucoisomerase (PGI), tagatose 6-phosphate 4-epimerase (TiT4E), and tagatose 6-phosphate phosphatase (T6P) was constructed to produce tagatose using starch as a substrate. In the catalytic system, αGP produced glucose 1-phosphate from starch and inorganic phosphorus ions, PGM converted glucose 1-phosphate to glucose 6-phosphate, PGI converted glucose 6-phosphate to fructose 6-phosphate, TiT4E converted fructose 6-phosphate to tagatose 6-phosphate, and T6P converted tagatose 6-phosphate to tagatose, with phosphorus ions released. Phosphorus ions were in balance throughout the whole reaction. In the catalytic system, αGP was derived from *Thermotoga maritima*, and the gene numbering on KEGG was TM1168; PGM was also derived from *Thermotoga maritima*, and the gene number on KEGG was TM0769; PGI was derived from *Clostridium thermocellum*, and the gene numbering on KEGG was Cthe0217; T4E was TiT4E, from the present invention; T6P was derived from *Archaeoglobus fulgidus*, and the gene numbering on KEGG was AF_0444. All the above enzymes were heterologously expressed in *E. coli* and purified.

In a 1.0 ml reaction system comprising 40 mM phosphate buffer (pH 7.0), 5 mM divalent magnesium ions, 1 U/ml αGP, 1 U/ml PGM, 1 U/ml PGI, 1 U/ml TiT4E, 1 U/ml T6P, and 150 g/L soluble starch, a catalytic reaction was carried out at 60° C. After 48 hours of reaction, the components in the reaction solution were detected using a high-performance liquid chromatography (HPLC) instrument equipped with a Bio-Rad HPX-87H column. The HPLC analyzer can be used to identify tagatose, glucose, glucose 1-phosphate or glucose 6-phosphate in the reaction solution (as shown in FIG. 5); and can be used to quantify tagatose, wherein the concentration of tagatose was proportional to the intensity of the characteristic peak of tagatose in the HPLC diagram; the mobile phase of HPLC was 5 mM dilute sulfuric acid.

Figure 1:
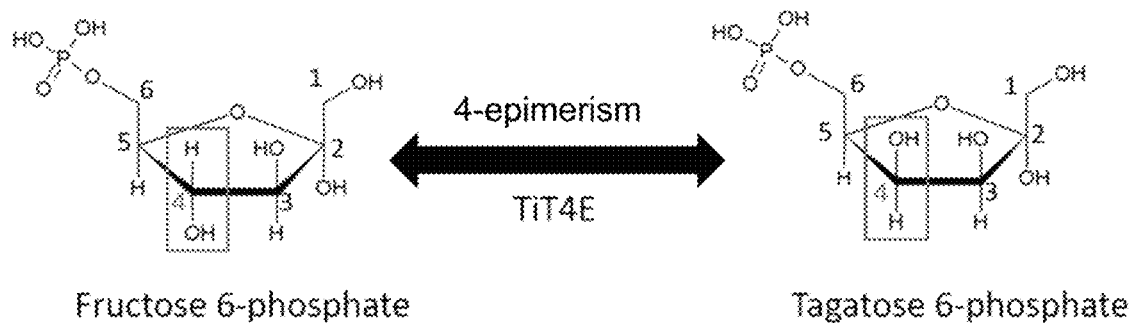
FIG. 1. A schematic diagram showing the conversion of fructose 6-phosphate to tagatose 6-phosphate, which involves the epimerization reaction of the 4-position carbon atom of fructose 6-phosphate.
Figure 5:
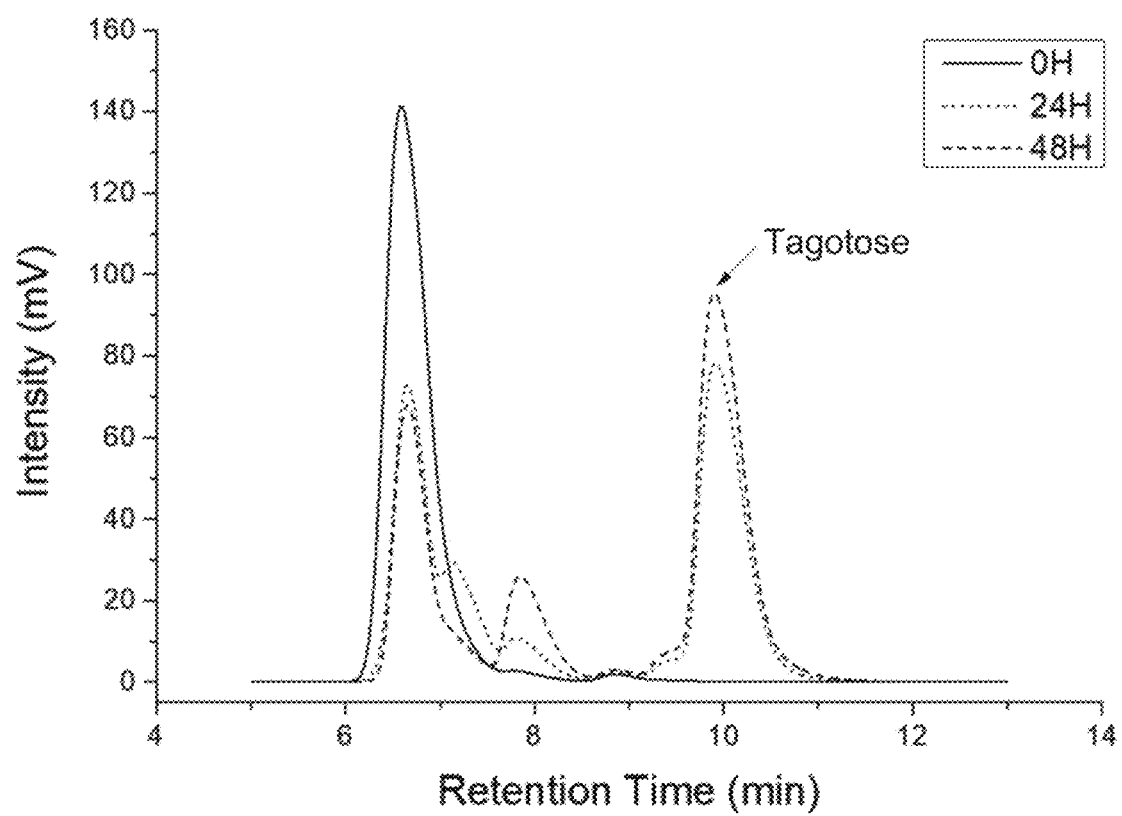
FIG. 5. TiT4E and α-glucan phosphorylase (αGP), phosphoglucomutase (PGM), phosphoglucoisomerase (PGI) and tagatose 6-phosphate (T6P) were used to catalyze starch to produce tagatose. The figure is a high-performance liquid chromatography (HPLC) diagram showing detection of the reaction liquid during the reaction, in which the arrow indicates the formation of tagatose.

As shown in FIG. 5, it can be seen that the concentration of tagatose increased with the increase of reaction time. After the reaction, the final concentration of tagatose was 83 g/L (FIG. 1), with a conversion rate of 55%.

As can be seen, TiT4E in the present invention had the activity of converting fructose 6-phosphate to tagatose 6-phosphate, and can be combined with other enzymes to construct an in vitro multi-enzyme molecular machine for the production of tagatose from starch.

The invention claimed is:

1. A method of using a tagatose 6-phosphate 4-epimerase (TiT4E) to catalyze mutual conversion between fructose 6-phosphate and tagatose 6-phosphate, wherein the tagatose 6-phosphate 4-epimerase is selected from the group consisting of:
   (a) a protein having the amino acid sequence set forth in SEQ ID NO: 1; or
   (b) a protein having an amino acid sequence of ≥90% identity to the amino acid sequence set forth in SEQ ID NO: 1, and having an activity of catalyzing mutual conversion between fructose 6-phosphate and tagatose 6-phosphate.

2. The method according to claim 1, wherein the tagatose 6-phosphate 4-epimerase (TiT4E) is derived from *Thermoanaerobacter indiensis*.

* * * * *